(12) United States Patent
DiMeo, Jr. et al.

(10) Patent No.: US 6,265,222 B1
(45) Date of Patent: Jul. 24, 2001

(54) MICRO-MACHINED THIN FILM HYDROGEN GAS SENSOR, AND METHOD OF MAKING AND USING THE SAME

(76) Inventors: Frank DiMeo, Jr., 126 Willow Spring, New Milford, CT (US) 06776; Gautam Bhandari, 38 Padanaram Rd., Apt. 27, Danbury, CT (US) 06811

( * ) Notice: Subject to any disclaimer, the term of this patent is extended or adjusted under 35 U.S.C. 154(b) by 0 days.

(21) Appl. No.: 09/231,277

(22) Filed: Jan. 15, 1999

(51) Int. Cl.$^7$ .................................................. G01N 7/00
(52) U.S. Cl. .......................... 436/144; 436/147; 422/83; 422/88; 73/23.2; 73/31.06
(58) Field of Search .................................. 436/144, 147, 436/148; 422/83, 88, 90, 91, 98; 73/23.2, 31.06

(56) References Cited

U.S. PATENT DOCUMENTS 3,732,076 * 5/1973 Toy et al. .
6,006,582 * 12/1999 Bhandari et al. ..................... 73/23.2

* cited by examiner

*Primary Examiner*—Lyle A. Alexander
(74) *Attorney, Agent, or Firm*—Oliver A. M. Zitzmann; Steven J. Hultquist

(57) ABSTRACT

A hydrogen sensor including a thin film sensor element formed, e.g., by metalorganic chemical vapor deposition (MOCVD) or physical vapor deposition (PVD), on a micro-hotplate structure. The thin film sensor element includes a film of a hydrogen-interactive metal film that reversibly interacts with hydrogen to provide a correspondingly altered response characteristic, such as optical transmissivity, electrical conductance, electrical resistance, electrical capacitance, magnetoresistance, photoconductivity, etc., relative to the response characteristic of the film in the absence of hydrogen. The hydrogen-interactive metal film may be overcoated with a thin film hydrogen-permeable barrier layer to protect the hydrogen-interactive film from deleterious interaction with non-hydrogen species. The hydrogen sensor of the invention may be usefully employed for the detection of hydrogen in an environment susceptible to the incursion or generation of hydrogen and may be conveniently configured as a hand-held apparatus.

46 Claims, 7 Drawing Sheets

MICRO-MACHINED THIN FILM HYDROGEN GAS SENSOR, AND METHOD OF MAKING AND USING THE SAME

GOVERNMENT RIGHTS IN INVENTION

This invention was made with Government support under Contract No. NAS8-98188 awarded by the National Aeronautics and Space Administration (NASA). The government has certain rights in this invention.

BACKGROUND OF THE INVENTION

1. Field of the Invention

The present invention relates to a micro-machined thin film hydrogen sensor device, and a method of making and using the same.

2. Description of the Related Art

Hydrogen gas is used in variety of applications ranging from semiconductor thin film processing to rocket fuel in the aerospace industry. The combustible nature of hydrogen however, makes its detection vitally important.

About one-half of all the sensors used to measure hazardous gases measure hydrogen. The bulk of these systems utilize as the detector element a Group VIIIB metal element (Ni, Pd, Pt) that is heated to catalytically oxidize the hydrogen, with the resulting change in heat load being the measured parameter for determination of the presence of hydrogen.

Sensors of such "hot wire" type have cross-sensitivity to other easily oxidized materials, such as alcohols and hydrocarbons. Such easily oxidized materials are common components of gases in a semiconductor-manufacturing environment, and in such application the result is frequent occurrence of false alarms.

Since the current generation of hot wire sensors require an oxidation reaction for operation, such sensors are unable to detect hydrogen when it is present in inert gas streams or environments which are not of a character to support oxidative reaction. This is a severe deficiency of such hot wire sensors and limits their applicability and utility.

It would be a significant advance in the art to provide a sensor overcoming the aforementioned deficiencies of current hot wire sensors.

Another class of sensors includes metal-insulator semiconductor (MIS) or metal-oxide- semiconductor (MOS) capacitors and field effect transistors, as well as palladium-gated diodes. In general however, these sensors are limited to detecting low concentrations of hydrogen.

Because hydrogen is used in such a wide variety of environments, it is desirable to have a sensor that will be reproducible and specific to hydrogen, even with varying concentration of background gases such as oxygen, water and other contaminants.

It is also desirable to have a solid state sensor that has no moving parts, has a response time on the order of seconds, would operate with minimum power consumption, does not require frequent calibration, and could be used in a hand-held portable instrument.

The disclosures of the foregoing references are hereby incorporated herein by reference in their entireties, together with the disclosures of the following pending United States patent applications: U.S. patent application Ser. No. 09/042, 698 filed Mar. 17, 1998 in the names of Gautam Bhandari and Thomas H. Baum for "Hydrogen Sensor Utilizing Rare Earth Metal Thin Film Detection Element, now U.S. Pat. No. 6,029,500" and U.S. patent application Ser. No. 09/081, 957 filed May 19, 1998 in the name of Glenn M. Tom for "Piezoelectric Quartz Crystal Hydrogen Sensor, and Hydrogen Sensing Method Utilizing Same, now U.S. Pat. No. 6,029,500."

It therefore is one object of the present invention to provide an improved hydrogen sensor.

It is another object of the invention to provide a hydrogen sensor that senses the presence of hydrogen in a reproducible and hydrogen-specific manner.

It is another object of the invention to provide a hydrogen sensor that senses the presence of hydrogen in a reproducible and hydrogen-specific manner, even with varying concentration of background gases such as oxygen, water and other contaminants.

It is yet another object of the present invention to provide a solid state hydrogen sensor that has no moving parts, has a response time on the order of seconds, operates with minimum power consumption, does not require frequent calibration, has a large dynamic detection range, and can be readily embodied as a hand-held portable instrument.

Other objects and advantages of the present invention will be more fully apparent from the ensuing disclosure and appended claims.

SUMMARY OF THE INVENTION

The present invention relates in one aspect to a hydrogen sensor, comprising a hydrogen-interactive thin film sensor element on a micro-hotplate structure.

The hydrogen-interactive thin film sensor element of such sensor may comprise a hydrogen-interactive thin film (i) arranged for exposure to an environment susceptible to the incursion or generation of hydrogen and (ii) exhibiting a detectable change of physical property when the hydrogen-interactive thin film is exposed to hydrogen. Such detectable change of physical property may comprise optical transmissivity, electrical resistivity, electrical conductivity, electrical capacitance, magneto-resistance, photoconductivity, and/or any other detectable property change accompanying the exposure of the thin film sensor element to hydrogen. The hydrogen sensor may further include a detector constructed and arranged to convert the detectable change of physical property to a perceivable output, e.g., a visual output, auditory output, tactile output, and/or auditory output.

In one preferred embodiment, the hydrogen-interactive thin film is overlaid by a hydrogen-permeable material protecting the rare earth metal thin film from deleterious interaction with non-hydrogen components of the environment being monitored, such as nitrogen, oxygen, ammonia, hydrocarbons, etc. The protective-overlayer may include a metal such as Pd, Pt, Ir, Rh, Ag, Au, Co, and/or alloys thereof.

The micro-hotplate structure in the sensor of the invention may be advantageously constructed and arranged for selectively heating the hydrogen-interactive thin film gas sensor element according to a predetermined time-temperature program, e.g., involving cyclic heating of the hydrogen-interactive thin film gas sensor element by the micro-hotplate structure.

The invention relates in another aspect to a hydrogen sensor device, comprising:
  a micro-hotplate structure;
  a hydrogen-interactive thin film gas sensor element on the micro-hotplate structure; and a detector for sensing a detectable change of physical property of the film in exposure to hydrogen and generating a correlative output indicative of hydrogen presence.

A power supply may be provided in such device and may be constructed and arranged for actuating the micro-hotplate structure during and/or subsequent to sensing the detectable change of physical property of the rare earth metal thin film in exposure to hydrogen, and/or for energizing the detector.

A further aspect of the invention relates to a method of fabricating a hydrogen sensor on a substrate, comprising: constructing on the substrate a micro-hotplate structure; and forming on the micro-hotplate structure a hydrogen-interactive thin film that in exposure to hydrogen exhibits a detectable change of at least one physical property, and wherein the hydrogen-interactive thin film is arranged to be heated by the micro-hotplate structure.

A still further aspect of the invention relates to a method of detecting hydrogen in an environment, comprising:

providing a hydrogen sensor device comprising a hydrogen-interactive thin film operatively coupled with a micro-hotplate structure for selective heating of the hydrogen-interactive thin film, with the hydrogen-interactive thin film being arranged for exposure to the environment and exhibiting a detectable change of physical property when the hydrogen-interactive thin film is exposed to hydrogen;

exposing the hydrogen-interactive thin film to the environment;

outputting said detectable change of physical property when the presence of hydrogen in the environment is detected; and selectively heating the hydrogen-interactive thin film by the micro-hotplate structure during and/or subsequent to detection of hydrogen in said environment, to enhance the performance of the hydrogen-interactive thin film for detection of hydrogen.

Other objects and advantages of the invention will be more fully apparent from the ensuing disclosure and claims.

DETAILED DESCRIPTION OF THE INVENTION, AND PREFERRED EMBODIMENTS THEREOF

Figure 1:
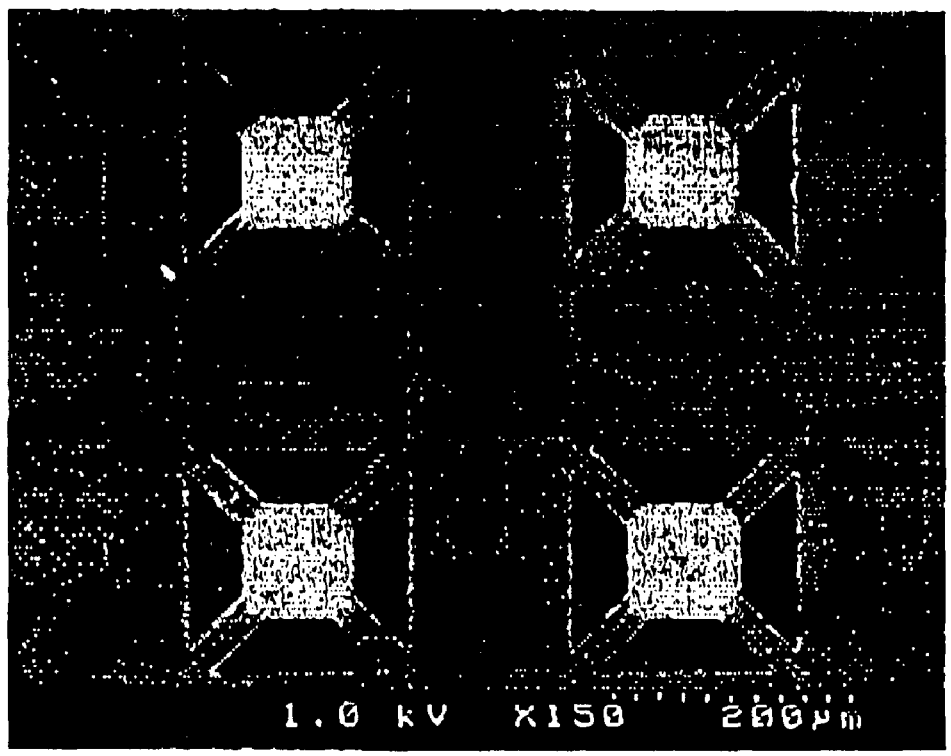
FIG. 1 is a scanning electron microscope (SEM) micrograph of a thin film sensor including a thin film sensor element deposited by metalorganic chemical vapor deposition (MOCVD) on a micro-hotplate structure.

The present invention relates to a hydrogen sensor integrating a thin film hydrogen sensor element with a micro-hotplate structure. The hydrogen sensor of the invention is a solid-state device that may be adapted in a variety of apparatus embodiments to accommodate the objects of the invention.

The micro-hotplate structure usefully employed in the practice of the present invention, in integration with the thin film hydrogen sensor element hereinafter more fully described, may be of a form as more fully described in the following references: U.S. Pat. No. 5,356,756 issued Oct. 18, 1994 to R. Cavicchi et al.; U.S. Pat. No. 5,345,213 issued Sep. 6, 1994 in the names of S. Semancik, et al; J. S. Suehle, R. E. Cavicchi, M. Gaitan, and S. Semancik, "Tin Oxide Gas Sensor fabricated using CMOS Micro-hotplates and In Situ Processing," IEEE Electron Device Lett. 14, 118–120 (1993); S. Semancik and R. E. Cavicchi, "The use of surface and thin film science in the development of advanced gas sensors," Appl. Surf. Sci 70/71, 337–346 (1993); R. E. Cavicchi, J. S. Suehle, K. G. Kreider, M. Gaitan, and P. Chaparala, "Fast Temperature Programmed Sensing for Microhotplate Gas Sensors," IEEE Electron Device Letters 16, 286–288 (1995); R. E. Cavicchi, J. S. Suehle, K. G. Kreider, B. L. Shomaker, J. A. Small, M. Gaitan, and P. Chaparala, "Growth of $SnO_2$ films on micromachined hotplates," Appl. Phys. Lett. 66 (7), 812–814 (1995); C. L. Johnson, J. W. Schwank, and K. D. Wise, "Integrated Ultra-thin film gas sensors," Sensors and Act B 20, 55–62 (1994); X. Wang, W. P. Carey, and S. S. Yee, "Monolithic thin film metal oxide gas sensor arrays with application to monitoring of organic vapors," Sensors and Actuators B 28, 63–70 (1995); N. R. Swart and A. Nathan, "Design Optimization of integrated microhotplates," Sensors and Act A 43, 3–10 (1994); and N. Najafi, K. D. Wise, and J. W. Schwank, "A micromachined thin film gas sensor," IEEE Electron Device Lett. 41 (10) (1994). The disclosures of such references are hereby incorporated herein by reference in their entireties, as is the disclosure of "F. DiMeo Jr., S. Semancik, R. E. Cavicchi et al., "MOCVD of $SnO_2$ on silicon microhotplate arrays for use in gas sensing application," Mater. Res. Soc. Symp. Proc. 415, 231–6 (1996).

The sensing mechanism of the hydrogen sensor device of the present invention is based on the reversible, hydrogen-induced transition from the metallic di-hydride compound to the semi-conducting tri-hydride compound, according to the following equation:

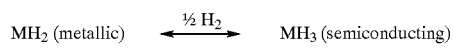

wherein M comprises the hydrogen-interactive thin film element. The hydrogen-interactive thin film element may comprise one or more thin films wherein at least one thin film is selected from the group consisting of rare earth metals, Group II elements or any combination thereof. The rare earth metal and the Group II element may be combined to form a Group II element doped rare earth metal thin film or an alloy thin film comprising the rare earth metal and the Group II element. Rare earth and alkaline earth hydride films are extremely oxophilic in nature, and may also interact with other atmospheric or environmental species in a manner that masks the hydrogen interaction. In order to obviate such deleterious interactions with non-hydrogen species, where the hydrogen sensor is intended to operate in environments containing same, it may be advantageous to overcoat the hydrogen-interactive thin film of the sensor with a protective film layer of a coating that is permeable to hydrogen, but is impermeable to the deleterious interaction species present in the environment. One such protective film layer material is palladium (Pd). Hydrogen is known to diffuse readily through a Pd film, while oxygen and nitrogen do not penetrate the Pd film, thus allowing the formation of the rare earth metal and/or Group II hydride without the formation of oxides and/or nitrides.

By way of specific example, in sensor devices constructed in accordance with the invention, including an yttrium (Y) sensor film overcoated with a Pd film layer, the sensor film was found to be sensitive to hydrogen in a nitrogen environment, to hydrogen in a pentane environment, and to hydrogen in an ammonia environment, thus demonstrating the selectivity of the sensing film in such environments.

The integration of such hydrogen-interactive sensor films with micro-hotplate structures in accordance with the present invention permits the selective heating of the sensor film by the micro-hotplate structure, thereby increasing the rate of interaction of the sensor film with any hydrogen gas in the environment being monitored, as well as increasing the rate of regeneration or recovery of the sensor film. Thus, the sensor film may be selectively heated during the active sensing operation so that the reaction of $YH_2 + \frac{1}{2}H_2 \rightarrow YH_3$ is increased, to thereby enhance the sensitivity of the hydrogen sensor device, and after the sensing is complete, the sensor film may be further heated to higher temperature to cause the reverse reaction $YH_3 \rightarrow YH_2 + \frac{1}{2}H_2$ to take place. The micro-hotplate may therefore be coupled with suitable power supply and cycle time controller circuitry, so that the micro-hotplate structure provides appropriate heating of the hydrogen-interactive sensor film for the desired monitoring operation. Such power supply and cycle time controller circuitry may for example be constructed and arranged for pulsed or variable cycle time operation, or according to a selected time-temperature schedule.

Such micro-hotplate structure heating of the hydrogen sensor film significantly enhances the operation of the sensor device of the invention, relative to a corresponding sensor device lacking the micro-hotplate structure. For example, in a sensor device lacking the micro-hotplate structure, for ambient temperature sensing of hydrogen gas, typical response times were on the order of 1 minute after exposure to $H_2$, but complete recovery after removal of the $H_2$ source from the sensor was on the order of hours. By contrast, heating of the sensor film by the micro-hotplate structure substantially improves both the response and recovery times of the sensor device. The micro-hotplate allows electrical measurement of the sensor film while controlling the temperature of the film, thus allowing the formation of the hydride in a highly effective manner.

The hydrogen-interactive sensor film may be readily formed on the micro-hotplate by any suitable deposition techniques, such as, for example, sputter deposition, solution deposition, metal-organic chemical vapor deposition (MOCVD), physical vapor deposition (PVD), and corresponding assisted vapor deposition processes, such as plasma-assisted MOCVD.

The preferred technique for forming the hydrogen-interactive sensor film on the micro-hotplate structure is by physical vapor deposition or chemical vapor deposition. If CVD is employed, then the individual micro-hotplates can be separately heated, in a self-lithographic process flow.

The micro-hotplate structure of the sensor device of the invention may be readily fabricated by micro-machining techniques, as for example based on complementary metal oxide semiconductor (CMOS) fabrication techniques.

One illustrative embodiment of sensor fabrication involves the following steps. A desired micro-hotplate array is designed and laid out, and may for example comprise 4, 8 or more individual micro-hotplate elements. This micro-hotplate array can then be fabricated in a commercial CMOS process using a facility such as the MOSIS system. The resulting micro-hotplate array is micro-machined and packaged. Next, the packaged chip can be placed in either a PVD or a CVD chamber and at least one thin metallic film of the hydrogen-interactive film material can be deposited on the hotplate elements of the micro-hotplate structure. With the appropriate electrical feedthroughs, the hotplate elements can be heated to improve the properties of the metal film deposition. Additionally, with appropriate electrical feedthroughs, the resistance of the deposited films can be monitored in situ and used as a feedback variable for the deposition process. For example, when a specific value of conductance is reached, the film will have a particular thickness, and the conductance value can be utilized for control purposes in the film formation step, to stop the film growth operation at the point that the deposited film reaches the desired thickness. This feedback deposition technique can be used for each of the hydrogen-interactive film and the optional protective overlayer film of hydrogen-permeable, extraneous species-impermeable material, to achieve a desired film thickness of each such layer of the sensor element.

Another embodiment would follow the same basic steps as described above, but with the thin metallic film of the hydrogen-interactive film material deposited on the hotplate elements of the micro-hotplate structure before micro-machining and packaging.

Another embodiment would follow the same basic steps as described above with the exception that an alternative process might be used to fabricate the micro-hotplate structure instead of the CMOS process. Such alternative process might substitute Pt or W for the Al metallization typically used in the CMOS process. In any of such embodiments, both the hydrogen-interactive film and the optional protective-overlayer film may be made of different thicknesses within the same array (over different ones of the multiple micro-hotplate elements) to cover a broader dynamic range of hydrogen detection capability. For example, a thinner protective-overlayer film of Pd on the hydrogen-interactive sensor film can be used to detect a lower concentration of hydrogen, while a thicker protective-overlayer film of Pd on the hydrogen-interactive sensor film can be used to detect a higher hydrogen concentration, since a higher concentration driving force is required for the diffusion of hydrogen through the thicker protective-overlayer film to occur, relative to the diffusion of hydrogen gas through a thinner protective-overlayer film.

The optimal operation temperature or temperatures of the hydrogen sensors of the invention may be readily empirically determined without undue experimentation, for specific sensing applications.

As a consequence of the rapid thermal rise and thermal fall times that are characteristic of temperatures for micro-hotplate operation, pulsed temperature operation can be advantageously employed in use of the hydrogen sensor device of the invention. For example, as alluded to hereinabove, the hydrogen interactive sensor films may be most sensitive to initial hydrogen exposure at one specific temperature, but require a higher temperature to be returned to their initial state (for subsequent active sensing operation). In such instance, it may be desirable to pulse the micro-hotplate periodically to refresh the hydrogen-interactive sensor film, thereby minimizing the effect of drift and improving long term stability of the device.

The present invention thus makes use of the fact that upon exposure to hydrogen, hydrogen-interactive thin films exhibit striking changes in physical properties, changing from metallic (conducting) to semiconducting phases. These phase changes are accompanied by changes in electrical resistivity, magneto-resistance and photoconductivity of the hydrogenated rare earth thin film.

The invention contemplates a wide variety of sensor devices and apparatus, as well as methodology which utilizes hydrogen-interactive thin films with which hydrogen is interactive to produce both a physical and chemical change in the properties of the hydrogen-interactive thin film.

In the preferred practice of the invention, as described briefly hereinabove, the hydrogen-interactive thin film is overlaid by a protective-overlayer which is hydrogen-permeable, but which is at least highly impermeable to reactive species that could otherwise deleteriously interact with the rare earth metal thin film and prevent it from producing the desired physical property change of the film incident to exposure of the film to hydrogen.

As used herein, the term "hydrogen-interactive thin film element" means one or more thin films wherein at least one thin film is selected from the group consisting of one or more rare earth metals, one or more Group II elements as well as alloys or combinations thereof.

As used herein the term "rare earth metal means a metal selected from scandium, yttrium, lanthanum, the lanthanides, and the actinides as well as alloys and combinations of such metals, and alloys and combinations of such metals with Group II elements, e.g., calcium, barium, strontium, magnesium and radium. The lanthanides are the 14 elements following lanthanum in the Periodic Table, viz., cerium, praseodymium, neodymium, promethium, samarium, europium, gadolinium, terbium, dysprosium, holmium, erbium, thulium, ytterbium and lutetium. The actinides are the elements of the Periodic Table having the atomic numbers 89 through 103 inclusive, viz., actinium, thorium, protactinium, uranium, neptunium, plutonium, americium, curium, berkelium, californium, einsteinium, fermium, mendelevium, nobelium and lawrencium.

The physical property of the hydrogen-interactive thin film that is altered in response to the presence of hydrogen may be the optical transmissivity of the film to optical radiation incident on the sensor element, electrical resistivity, electrical conductivity, magnetoresistance, photoconductivity, electrical capacitance, or any other physical and/or chemical properties that are changed in exposure of the hydrogen-interactive thin film to hydrogen. The change in physical property of the hydrogen-interactive thin film is readily monitored, by appropriate detector and output components, to provide an output indicative of the presence of hydrogen in the environment to which the hydrogen-interactive thin film of the sensor is exposed.

The aforementioned changes in properties of hydrogen-interactive thin films, incident to their exposure to hydrogen, result from a chemical equilibrium between the dihydride and trihydride forms of such films. When hydrogen is present, a dynamic equilibrium exists between the two forms and the physical and optical changes can be quite dramatic.

For example, in the presence of hydrogen, noble metal (e.g., Pd, Pt) overcoated Y reacts to form the dihydride ($YH_2$). Further exposure to hydrogen results in the formation of the trihydride $YH_3$. This second step occurs at room temperature (e.g., about 25 degrees Centigrade) and ambient pressure (e.g., about 1 atmosphere) and is completely reversible. The formation of $YH_2$, on the other hand, is essentially irreversible at room temperature and ambient pressure, as a result of its relatively large heat of formation (−114 kJ/mol H) compared with the equilibrium step (−41.8 kJ/mol H or −44.9 kJ/mol H). This process is illustrated in the following formula:

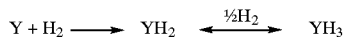

The transition of the optically reflecting rare earth dihydride to the optically transparent rare earth trihydride is a chemical change with electronic origins. The dark blue reflecting phase of $YH_2$ is metallic, whereas the transparent phase ($YH_3$) is semiconducting with a direct band gap of 1.8 eV. This change of state—from metallic to semiconducting—can therefore be readily quantified by measuring the resistance of the film under hydrogen exposure conditions. Resistance measurements allow the correlation of the optical and electrical behavior of the films.

As a consequence of the ability of micro-hotplates to localize high temperature heating to microscopic regions of the device structure, the sensors of the present invention can utilize elevated temperatures to enhance the hydrogen sensing operation without the dangers of hydrogen ignition that have plagued the prior art "hot wire" sensors described in the Background section hereof.

Further, the temperature control capability of the micro-hotplate structure permits the thermal management of the sensor in a highly effective and efficient manner. Qualitatively the rare earth dihydride to trihydride transition is an exothermic chemical reaction (negative ΔG: −41.8 kJ/mol H or −44.9 kJ/mol H). Thus, the micro-hotplate structure can be selectively actuated and controlled to provide appropriate temperatures favorable to hydrogen gas sensing.

While we do not wish to be bound by any theory as regards the specific mode or mechanism of behavior of the rare earth thin film sensors in accordance with the present invention, it is believed that a metal-insulator transition rather than a structural phase change causes the observed physical properties transformation.

The selectivity exhibited by hydrogen-interactive thin films allows, for the first time, fabrication of inexpensive hydrogen sensors that can be deployed in large numbers to remotely monitor hydrogen levels over large areas. Furthermore, hydrogen-interactive thin films can operate in an industrial or manufacturing environment containing trace organic vapors. We are not aware of any existing hydrogen sensing technologies having these attributes.

Hydrogen-interactive thin films can be coated with materials such as palladium or platinum to provide an effective barrier to oxidation, yet enable hydrogen to diffuse through to the rare earth thin film, thereby acting as a selective membrane for hydrogen in the sensor element.

The deposition of hydrogen-interactive thin films on the micro-hotplate substrate may be readily carried out using at least one organometallic precursor of the rare earth metal or the Group II element that thermally decomposes to the metal hydride or elemental metal in a reducing environment of hydrogen. Under some conditions, the direct formation of rare earth metal hydride materials may be realized.

The invention enables a hydrogen detection system to be constructed for monitoring an extended or remote area region for the incursion or generation of hydrogen therein. The hydrogen detection system may include a multiplicity of rare earth metal thin film/micro-hotplate detector devices each of which (i) is arranged for exposure to a specific individual locus of the extended area region and (ii) exhibits a detectable change of physical property, e.g., optical transmissivity, electrical resistivity, electrical conductivity, electrical capacitance, magneto-resistance and/or photoconductivity, when the hydrogen-interactive thin film of the detector device is contacted with hydrogen gas at such locus.

The hydrogen detection system described in the preceding paragraph may be constructed and arranged so that different physical properties are detected when multiple detector devices are contacted with hydrogen gas at different loci of the extended area region.

The hydrogen sensor of the invention is readily fabricated by forming on the micro-hotplate substrate a hydrogen-interactive thin film which is responsive to contact with hydrogen by exhibiting a detectable change of physical property, and coupling the thin film with means for exhibiting the detectable change of physical property when the hydrogen-interactive thin film is exposed to hydrogen.

The means for exhibiting the detectable change of physical property when the hydrogen-interactive thin film is contacted with hydrogen gas, may for example comprise a colored substrate, whereby the detectable change of physical property entails a change from opacity to transparency when the hydrogen-interactive film is contacted with hydrogen gas or a change in color as determined by the colored layer in close proximity to the hydrogen sensitive layer (lanthanum hydride film) in its transmissive form. By such arrangement, the colored substrate is obscured in the absence of hydrogen, and rendered visible when hydrogen is present and converts the formerly opaque film to a transparent film.

The means for exhibiting the detectable change of physical property when the hydrogen-interactive thin film is contacted with hydrogen gas, may include suitable circuit means for signal processing the change of physical property and generating an output indicative of the presence or absence of hydrogen gas.

In the preferred practice of the invention, the hydrogen-interactive thin film is formed on the substrate by a technique such as physical vapor deposition, chemical vapor deposition, sputtering, solution deposition, focused ion beam deposition, electrolytic plating, or electroless plating. The hydrogen-interactive thin film may also be separately and discretely formed as an independent element, remotely from the micro-hotplate structure, and subsequently secured or placed on the micro-hotplate structure, to form the integrated sensor.

Most preferably, the hydrogen-interactive thin film is formed on the substrate by physical vapor deposition, or alternatively by chemical vapor deposition, e.g., by liquid delivery chemical vapor deposition, using an organometallic precursor that thermally decomposes to the metal hydride or elemental metal in a reducing environment of hydrogen.

The hydrogen-interactive thin film in the sensor may in one embodiment comprise a rare earth metal thin-film. The rare earth metal thin film may include a rare earth metal component such as a trivalent rare earth metal, e.g., yttrium or lanthanum, that is reactive with hydrogen to form both metal dihydride and metal trihydride reaction products, wherein the metal dihydride and metal trihydride reaction products have differing physical properties. The physical property change may for example include an optical transmissivity change, such as a change of optical opacity to optical transparency when the rare earth metal thin film is contacted with hydrogen gas. The physical property change may comprise a change from a metallic state to a semiconducting state, whereby the step of monitoring the physical property to determine the presence of hydrogen gas in the environment may be carried out by monitoring the electrical resistance, conductance, capacitance, or other electrical property of the rare earth metal thin film.

The rare earth metal thin film in the broad practice of the invention may suitably comprise at least one metal selected from the group consisting of: scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium, alloys thereof, and alloys containing one or more of such metals alloyed or doped with a suitable dopant component such as copper, cobalt, iridium, magnesium, calcium, barium, strontium, etc.

The hydrogen-permeable material of the protective hydrogen-permeable barrier layer may suitably comprise a metal such as Pd, Pt, Ir, Ag, Au, Co, Al and/or alloys thereof.

As a further variation, the hydrogen-permeable protective overlayer may be formed of alternating material layers. The material layers may be formed of Pd, Ir and/or Pt. As used herein, the term "thin films" will be understood as broadly referring to films having a thickness of less than about 1,000 microns.

In the use of hydrogen-interactive thin films in the practice of the invention for hydrogen sensing applications in which the thin film will or may encounter oxidizing species in the environment being monitored for hydrogen, such as oxygen, moisture (relative humidity), nitrogen oxides, carbon oxides, etc., it is advantageous to coat or encapsulate the hydrogen-interactive thin film with a hydrogen-permeable protective material that prevents such oxidizing species, as well as other deleterious species in the environment, from contacting the hydrogen-interactive thin film.

The protective material may for example absorb oxygen and allow diffusion of hydrogen through the protective material to the rare earth metal thin film. Alternatively, the protective material may be impermeable to oxygen and/or other oxidizing species.

The protective material when present as an overlayer coating or encapsulant should be continuous and atomically dense in order to provide an effective barrier against oxidation. The thickness of the overlayer may be readily selected to minimize oxygen permeation while maximizing the response of the hydrogen-interactive thin film to hydrogen.

In one embodiment of the present invention in which a protective material overlayer is employed, the overlayer may be formed of a metal such as Pd, Pt, Ir, or alloys or combinations thereof with one another or with other metal species. Particularly useful alloys for such protective material overlayers include Pd—Ag (20%).

The CVD process when used to form the hydrogen-interactive thin film on the substrate, may employ bubbler delivery or liquid delivery with subsequent flash vaporization, using a suitable precursor or source compound, to generate a precursor vapor which is transported to the heated micro-hotplate substrate for decomposition to form the desired hydrogen-interactive film. Such precursors must be robust and volatile at the temperature of vaporization, yet they must decompose cleanly and efficiently on the substrate.

Particularly preferred precursors for rare earth metal thin film formation by CVD in the practice of the invention include tris(cyclopentadienyl)lanthanum, tris(cyclopentadienyl)yttrium, β-ketoamine complexes of lanthanum, β-ketoamine complexes of yttrium, β-diiminate complexes of lanthanum, β-diiminate complexes of yttrium; lanthanum amides, and yttrium amides.

Suitable precursors may be readily determined within the skill of the art by screening techniques conventionally used in the art of CVD formation of thin films, including thermogravimetric analysis (TGA) and differential scanning calorimetry (DSC) analysis. For example, such simultaneous thermal analysis (STA) studies under Ar and vacuum may be conducted to screen candidate precursors for suitable thermal stability and transport properties.

The STA studies are suitably conducted under conditions simulating CVD conditions, e.g., under a flow of $H_2$ (5%) diluted with argon to provide data for predicting the major decomposition pathway(s) of the candidate precursors.

This combination of tests allows for rapid screening of a number of potential precursors, and also allows the study of the effect of other species present in the CVD process, e.g., reducing agents such as $NH_3$, on the decomposition pathway.

For example, preferred hydrogen-interactive material thin films are from about 50 to about 2000 nm thick, more preferably from about 50 to about 200 nm thick, with a protective layer when present having a thickness of from about 2 to about 1000 nm, and more preferably from about 2 to about 100 nm, e.g., a 20 nm thick protective layer of a material such as Pd on a rare earth metal thin film of 100 nm thickness. The protective overlayer is preferably thick enough to adequately protect the sensor from oxidation and thin enough to leave unchanged the properties being monitored in the operation of the device.

The protective overlayer may be deposited or formed over the hydrogen-interactive thin film in any suitable manner, including spraying, solution deposition, dipping, chemical vapor deposition, physical vapor deposition, focused ion beam deposition, sputtering, etc. Generally, the methods described hereinabove for formation or coating of the hydrogen-interactive thin film in the first instance may also be used for forming the protective overlayer thereon, and vice versa.

The protective overlayer may be formed of any suitable material of construction, which is suitably effective to prevent chemical reaction or sorption processes from occurring that would preclude the efficacy of the hydrogen-interactive thin film for hydrogen sensing.

Although the protective overlayer material is typically in the form of a film that is formed directly on the underlying hydrogen-interactive thin film, it is possible within the broad scope of the present invention to utilize a protective material such as a free-standing film or a membrane that is in spaced relationship to the hydrogen-interactive thin film.

For example, the protective material may comprise a membrane that is permselective for hydrogen only. The membrane may thus form a cell within which the hydrogen-interactive thin film is deployed.

The protective overlayer material may for example be a metal, a polymeric film material, a vitreous or ceramic material, etc. Examples of useful metals include Pd and other noble metals such as Pt, Ir, etc.

In the preferred practice of the invention, Pd is utilized as a protective overlayer material, and may be usefully deposited on the hydrogen-interactive thin film by chemical vapor deposition from a corresponding precursor.

Examples of precursors that may be used as source compositions for deposition of Pd by CVD include $Pd(hfac)_2$, $Pd(allyl)_2$ and CpPd(allyl).

In a preferred aspect of the invention, the thickness of a Pd or other noble metal protective overlayer is selected to optimize the response of the films to hydrogen. The overlayer is desirably continuous and atomically dense in order to provide an effective barrier against oxygen. The thickness of the protective layer is strongly dependent on the average roughness of the underlying film. The smoother the topography of the underlying hydrogen-interactive, the thinner the protective overlayer can be to provide effective coverage.

Pd absorbs approximately nine hundred times its volume of hydrogen gas. Although such absorption is reversible and highly selective for hydrogen, excessive dissolution of hydrogen in the Pd protective overlayer may slow its diffusion to the underlying hydrogen-interactive thin film. Such hydrogen dissolution may also result in slow "re-zeroing" of the sensor after detection of hydrogen, due to slow rates of desorption, and the thermal actuation and output of the micro-hotplate are desirably utilized to compensate for the system "restoration delay" that would otherwise result in the absence of thermal recovery operation by the micro-hotplate structure.

Both Pt and Ir absorb hydrogen and allow hydrogen to diffuse through them and can readily be used in place of Pd. A number of Pd-rich alloys also absorb hydrogen, e.g., Pd—Ag (20%). Membranes of this alloy do not undergo the volume expansion and cracking that is sometimes observed for pure Pd and that may limit the use of such pure material. Pd-rich alloy membranes are used industrially and may be advantageously employed in the broad practice of the present invention.

Rare earth metal alloys of magnesium are also useful as the hydrogen-interactive sense layer. The overall optical transmission rate of a rare earth-magnesium alloy hydride is higher than that of the pure metal hydride. The heat of formation of magnesium hydride (−33 kJ/mol H) is similar to that of rare earth hydrides (c.a. ~40 kJ/mol H) and the uptake of hydrogen by these alloys is reversible. In addition, the band gap of magnesium hydride is large enough that it forms a transparent hydride.

Alloying Gd with Mg to form the hydrogen-interactive sensing layer yields a number of benefits. The alloyed films display much higher transmittance than pure Gd films. In Gd—Mg (30%) alloys maximum transmittance is achieved at pressures well below 0.1 bar. This characteristic makes the alloyed film very sensitive to hydrogen. The slope of total transmittance vs. $P[H_2]$ curve, below 1 bar, changes considerably with the concentration of Mg in the film. Alloying with a suitable metal, therefore, permits the sensory response of the film to be selectively "engineered" for specific concentrations of hydrogen in the product sensor device.

Alloying also increases the transmission ratio (i.e., transmission of hydrided film/transmission of dehydrogenated film) to over 3000. This is due to the virtual elimination of all residual transmission in the visible window. Residual transmission is typically small (c.a. 1.5%) and of indeterminate origin. It is observed when samples exposed to hydrogen are allowed to desorb in air. Alloying with magnesium shifts the transmission window to shorter wavelengths while gradually reducing the % transmission. For Gd—Mg alloy films containing 30 at. % Mg, the maximum transmission of a 200 nm layer is 0.01%. These properties make the Gd—Mg composition useful as an active layer material to form a highly sensitive thin film sensor.

Alloys containing Mg at concentrations higher than 50 at. % exhibit three different optical states: transparent, absorbing, and reflecting; rather than just transparent and reflecting. This observation can be exploited to provide another intermediate sensory response, and enables the use of such alloys in tri-state optical switches.

The foregoing examples illustrate the utility of engineering the band gap and free energy of the rare earth dihydride to trihydride transition, and such modification may be effected in the broad practice of the invention by the addition to the hydrogen-interactive thin film of a wide variety of potentially suitable dopants.

The specific dopant employed, and its concentration, are appropriately selected to enable the formation of an alloy hydride that has a band gap large enough to be transparent in the visible region or otherwise appropriately constituted for a detectable change of property or properties in exposure to hydrogen. Ideally, the dopant will also render the dihydride to trihydride equilibrium thermodynamically neutral. Mg, Ca, Ba, Sr, Al, Ir and Co are potentially useful dopant species for such purpose. Transition metal elements such as Co and Ir form a variety of stoichiometric and non-stoichiometric hydride species and may be particularly useful in a given end use application.

In one embodiment of the invention, the hydrogen-interactive thin film may be layered comprising one or more thin films wherein at least one thin film is selected from the group consisting of rare earth metals, Group II elements or any combination thereof. The rare earth metal and the Group II element may be combined to form a Group II element doped rare earth metal thin film or an alloy thin film comprising the rare earth metal and the Group II element. This embodiment represents another technique for selectively varying the response characteristics of the hydrogen-selective thin film to achieve a desired sensory sensitivity for the hydrogen-selective thin film sensor.

Doping techniques are well known by those skilled in the art. Doping may include the addition of at least one element impurity to the hydrogen-interactive thin film or the deposition of a thin film adjacent to the hydrogen-interactive thin film so as to produce a hydrogen-interactive thin film with a desired characteristic.

In another embodiment of the invention, the protective overlayer on the hydrogen-interactive thin film may be layered, with alternating constituent layers of overlayer materials such as Pd, Ir, Rh, Ag, Au, Co, Pt and/or alloys thereof, as another technique for selectively varying the response characteristics of the protective overlayer to achieve a desired sensory sensitivity for the hydrogen-selective thin film sensor.

For example, a sensory Y and/or Gd film may be formed with alternating protective overlayers of elements such as Pd and Pt, to provide maximum sensitivity and capability over a wide range of hydrogen concentration. The Pd/Pt interlayers in such a structure act as hydrogen storage layers as well as oxygen barrier layers, thereby enhancing the sensitivity of the film. Such a construction also allows reduction of the thickness of the top layer well below 50 Å.

In another embodiment of the invention, the hydrogen-interactive thin film sensor may comprise a multi-layered hydrogen-interactive element wherein, a first deposited thin film comprising Mg is deposited adjacent to the microhotplate structure and a second thin film comprising Y is deposited adjacent to the first deposited Mg thin film wherein, the multilayered hydrogen interactive element comprising a first Mg thin film and a second Y thin film would be coated with a Pd protective overlayer.

In a preferred embodiment of the invention, the hydrogen-interactive thin film sensor may comprise a hydrogen-interactive element wherein, a thin film of Y is deposited adjacent to the microhotplate structure, and a Pd protective overlayer is deposited adjacent to the hydrogen interactive element.

In another preferred embodiment of the invention, the hydrogen-interactive thin film sensor may comprise a hydrogen-interactive element wherein, a thin film consisting of 30 At % Mg and 70 At % Y is deposited adjacent to the microhotplate structure, and a Pd protective overlayer is deposited adjacent to the hydrogen-interactive element.

The foregoing illustrative materials, Pd, Ir, Rh, Ag, Au, Co, Pt and/or alloys thereof, may be deposited to form the sensor device by any suitable method, with CVD being generally preferred. A wide variety of useful precursors for such CVD formation of the material on a given substrate or intermediate structure of the sensor may be readily determined within the skill of the art and without undue experimentation.

Examples of potentially useful precursors for Mg and Ir include $Mg(thd)_2$ and $(COD)Ir(hfac)$, respectively.

Precursors for Al include, for example, the dimethylethyl amine adduct of alane ($AlH_3$) or dimethylaluminumhydride (DMAH), an air sensitive volatile liquid that is useful to deposit high quality aluminum films.

Cobalt precursors include cobalt beta-diketonates such as $Co(thd)_2$ or $Co(hfac)_2$.

Referring now to the drawings, FIG. 1 is a scanning electron microscope (SEM) micrograph of a thin film sensor including a thin film sensor element deposited by metalorganic chemical vapor deposition (MOCVD) on a microhotplate structure. The micro-machined sensor platforms define a 4-element gas-sensing array in which the active elements are shown as light gray regions.

Figure 2:
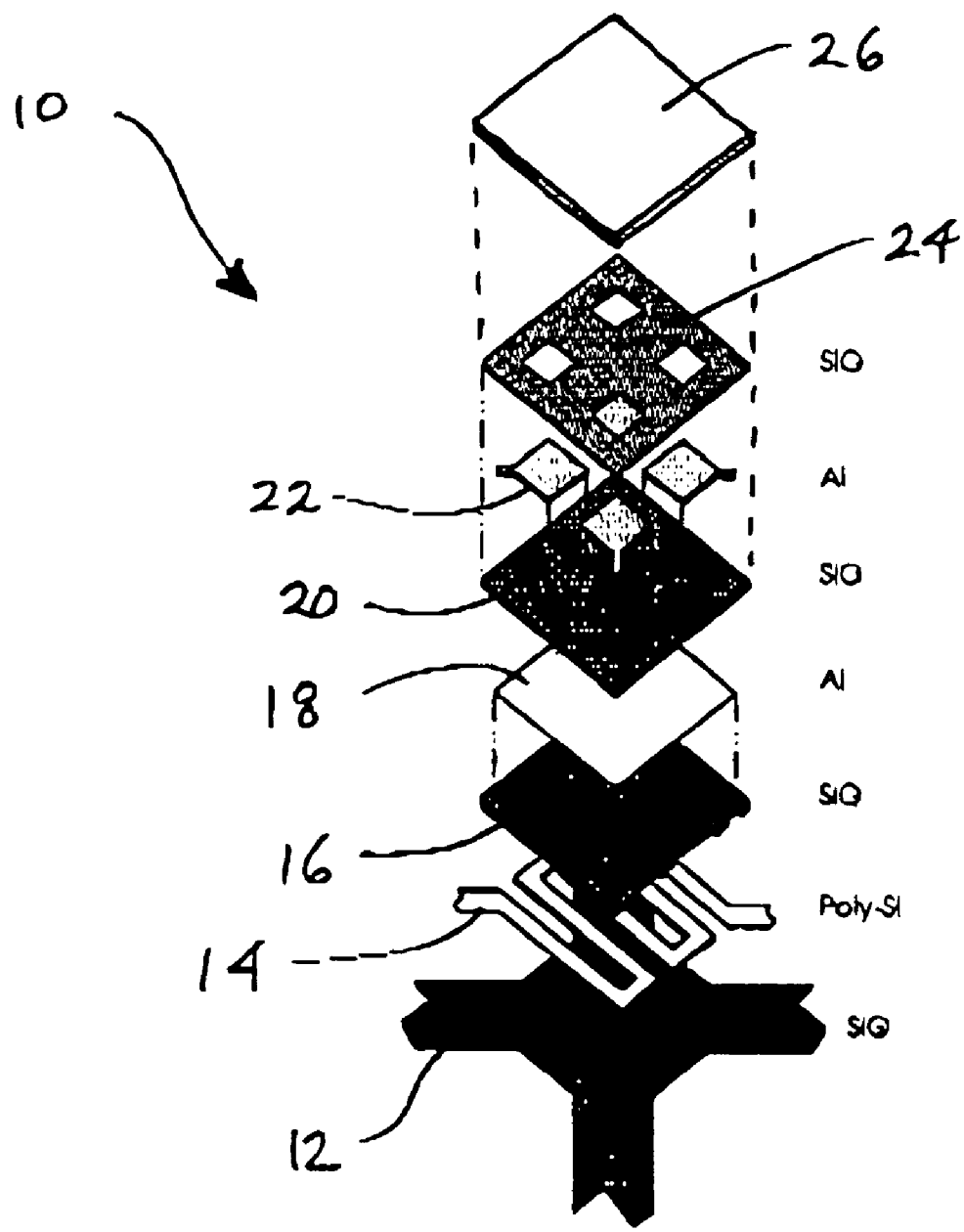
FIG. 2 is an exploded view of constituent layers of a hydrogen sensor according to one embodiment of the present invention.

FIG. 2 is an exploded view of constituent layers of a hydrogen sensor 10 of the type shown in FIG. 1, and constructed according to one embodiment of the present invention. The lowermost layer 12 is formed of silicon dioxide ($SiO_2$) and defines a suspended membrane or microbridge. The next succeeding layers include polycrystalline silicon heating element 14, silicon dioxide insulating layer 16, conductive heat distribution plate 18 formed of aluminum, silicon dioxide insulating layer 20, four aluminum contact pads 22, and silicon dioxide insulating layer 24 with four openings therein communicating respectively with the four aluminum contact pads 22. The layers 12, 14, 16, 18, 20, 22 and 24 corporately constitute the micro-hotplate structure of the hydrogen sensor.

Overlying the silicon dioxide insulating layer 24 is the thin film sensor layer 26. The thin film sensor layer 26 may comprise only a rare earth metal thin film, or such rare earth metal thin film may be optionally overlaid with a hydrogen-permeable protective barrier layer thin film.

The micro-hotplate structure of the hydrogen sensor shown in FIG. 2 may be constructed as more fully described in U.S. Pat. No. 5,356,756 to R. Cavicchi, et al. Typical physical characteristics are listed in Table 1 for the micro-hotplate structure of FIG. 2 comprising the thermally isolated, suspended resistive heater, the thin film thermometer, and the four contact pads for measuring the conductance of the active layer.

TABLE 1

| Typical Micro-hotplate Physical Characteristics | |
| --- | --- |
| Suspended Mass | ~0.2 µg |
| Suspended Area | 100 µm × 100 µm, |
| Maximum Surface Temperature | 550° C. |
| Thermal rise time, fall time | 1–3 ms, 3–4 ms |
| Continuous-use Power Consumption | 60 mW |

Figure 3:
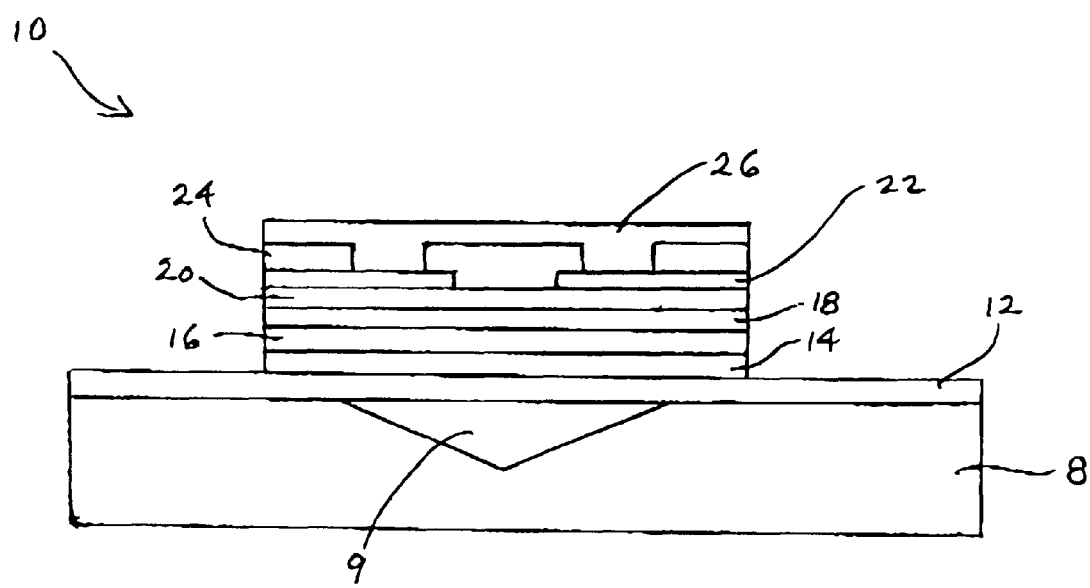
FIG. 3 is a schematic cross-sectional elevation view of a hydrogen sensor according to one embodiment of the present invention showing the constituent layers of the structure on a silicon substrate.

FIG. 3 is a schematic cross-sectional elevation view of a hydrogen sensor 10 according to one embodiment of the present invention showing the constituent layers of the structure on a silicon substrate 8. In the FIG. 3 device, elements corresponding to those of FIG. 2 are correspondingly numbered.

In the device structure of FIG. 3, the silicon dioxide layer 12 is overlaid in sequence by polycrystalline silicon heating element layer 14, silicon dioxide insulating layer 16, conductive (Al) heat distribution plate layer 18, silicon dioxide insulating layer 20, Al contact pads 22, silicon dioxide insulating layer 24. The silicon substrate 8 is removed from the pit 9 therein, below the silicon dioxide, thus creating a suspended microbridge. The suspended structure is overlaid with the thin film sensor layer 26, including a rare earth metal thin film optionally overlaid with a hydrogen-permeable protective barrier layer thin film to prevent oxygen and other oxidizing species from contacting the rare earth metal thin film.

Figure 4:
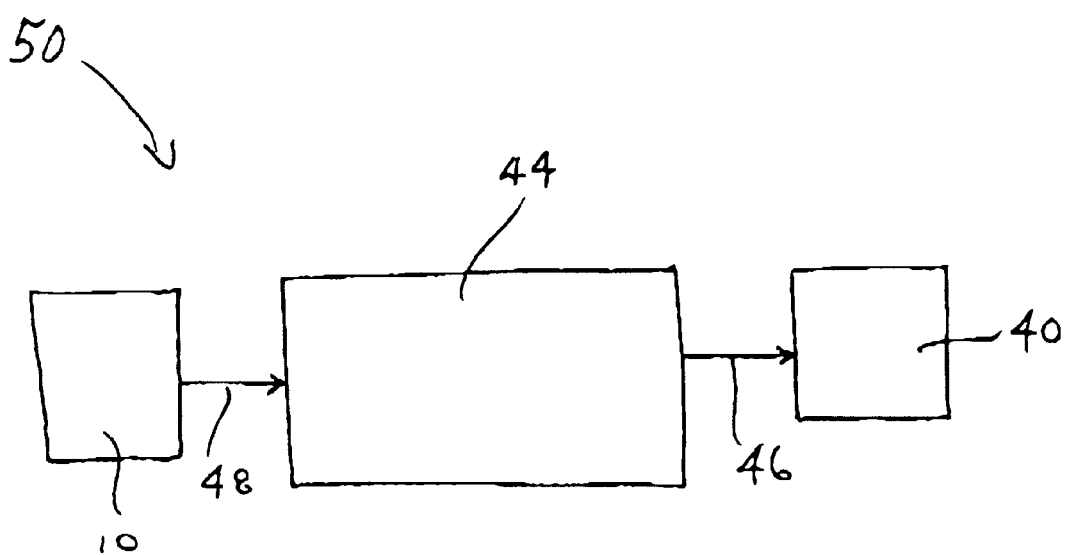
FIG. 4 is a schematic representation of a hydrogen sensor apparatus according to one embodiment of the invention.

FIG. 4 is a schematic representation of a hydrogen sensor apparatus 50 according to one embodiment of the invention. The hydrogen sensor apparatus 50 includes a hydrogen sensor device 10 that may be constructed and arranged as described hereinabove.

The hydrogen sensor device 10 is connected by signal transmission line 48 to the central processor unit 44, which may comprise microprocessor or computer control elements for actuation, monitoring and control of the hydrogen sensor device. The central processor unit 44 processes the signal carried by signal transmission line 48, and produces an output signal that is transmitted in signal transmission line 46 to output device 40, which produces an output that is indicative of the presence or absence of hydrogen in the environment to which the sensor is exposed.

The output of the central processor unit 44 may include any perceivable output, such as auditory output, visual output, tactile output (as for example when the hydrogen sensor apparatus is adapted to be worn on the body of a user, and the central processor unit comprises a vibrator imparting vibratory sensation to the user's body when hydrogen is detected in the environment, such as may be useful in environments where auditory or visual outputs are not readily perceivable.

In lieu of producing an output which is perceivable, the central processor unit 44 may be programmed to actuate means for eliminating hydrogen from the environment being monitored, as for example a sweep gas flushing operation to purge the environment of the hydrogen gas.

It will be recognized that the hydrogen sensor may be constructed so that the rare earth metal thin film is arranged in hydrogen permeation exposure to the environment being monitored. For example, the active face of the sensor defined by the layer 26 in the FIGS. 2 and 3 drawings may be contained in a sensing head which is insertable into a specific gas environment susceptible to the incursion or in situ generation of hydrogen therein.

The CPU 44 may be programmably arranged to maintain an appropriate monitoring status indicative of the presence or absence of hydrogen gas in the environment being monitored. The CPU may include an electrical resistivity monitor communicating by signal transmission line 48 with the hydrogen sensor device 10, to monitor the change in electrical resistivity of the film element incident to the introduction of hydrogen into contact with the hydrogen sensor device 10, and to responsively generate a corresponding output signal.

Figure 5:
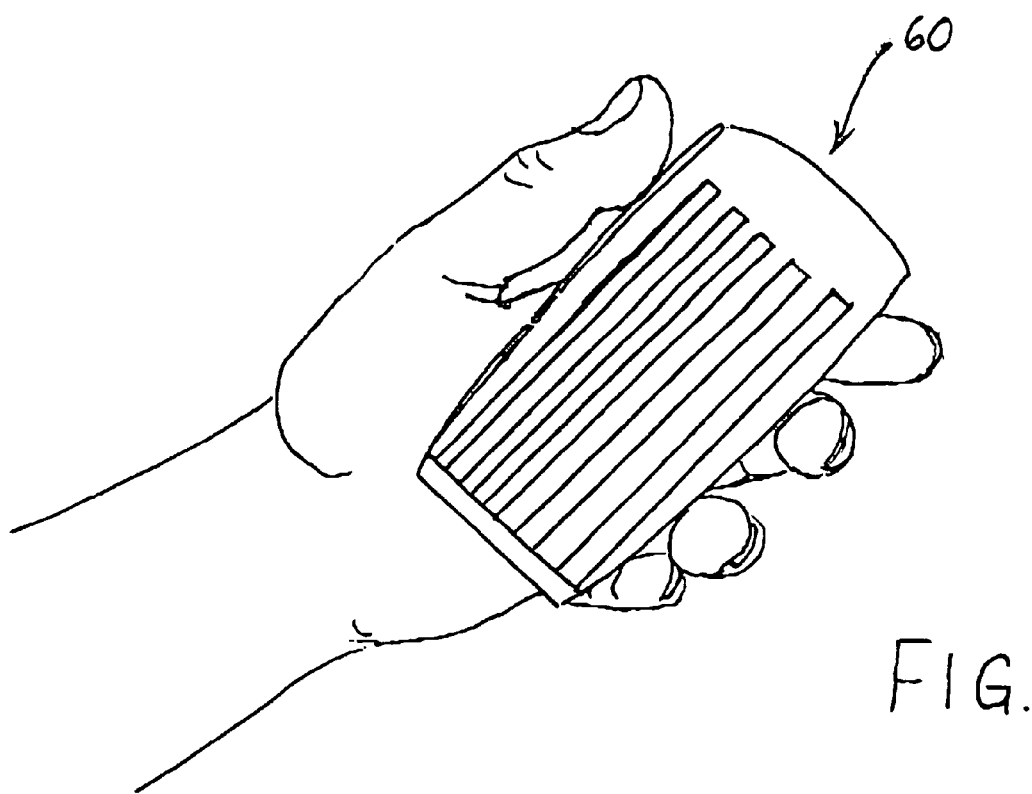
FIG. 5 is a perspective view of a hand-held hydrogen sensor apparatus according to one embodiment of the present invention.

FIG. 5 is a perspective view of a hand-held hydrogen sensor unit 60 according to one embodiment of the present invention, comprising the sensor apparatus in housing adapted for manual transport and deployment. The sensor unit 60 may for example be constructed with an audible alarm indicating the presence of hydrogen gas in the environment being monitored. Such hydrogen sensor unit may be conveniently fabricated as a solid-state battery-powered device, with a very small weight.

It will be appreciated that the hydrogen sensor of the present invention may thus be provided in a wide variety of potentially useful configurations, for a corresponding variety of hydrogen sensing applications.

Figure 6:
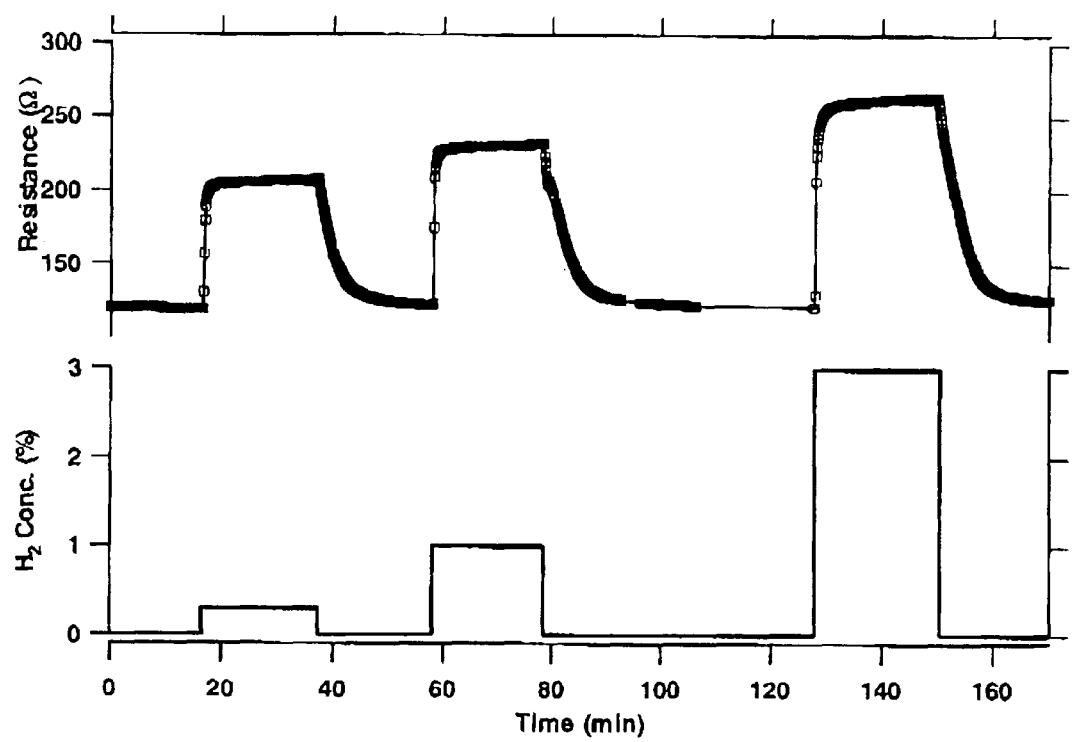
FIG. 6 is a graph showing the resistance response of a palladium/yttrium micro-hotplate sensor as a function of time when exposed to various concentrations of hydrogen in a background gas of 1 atmosphere of nitrogen.

FIG. 6 is graph of the response of a $H_2$ sensor including a 15 nm thickness of palladium deposited on 300 nm of yttrium, overlaid on a suspended microhotplate structure. The top panel of the graph shows the measured resistance of the sensing film as a function of time, and the bottom panel of the graph shows how the concentration of $H_2$ was varied with time. The testing was done at atmospheric pressure, in a nitrogen ambient environment. The microhotplate element was held at a temperature of ~400° C. There is rapid increase in resistance when $H_2$ is introduced to the sensor, and magnitude of the response increases with increasing $H_2$ concentration.

Figure 7:
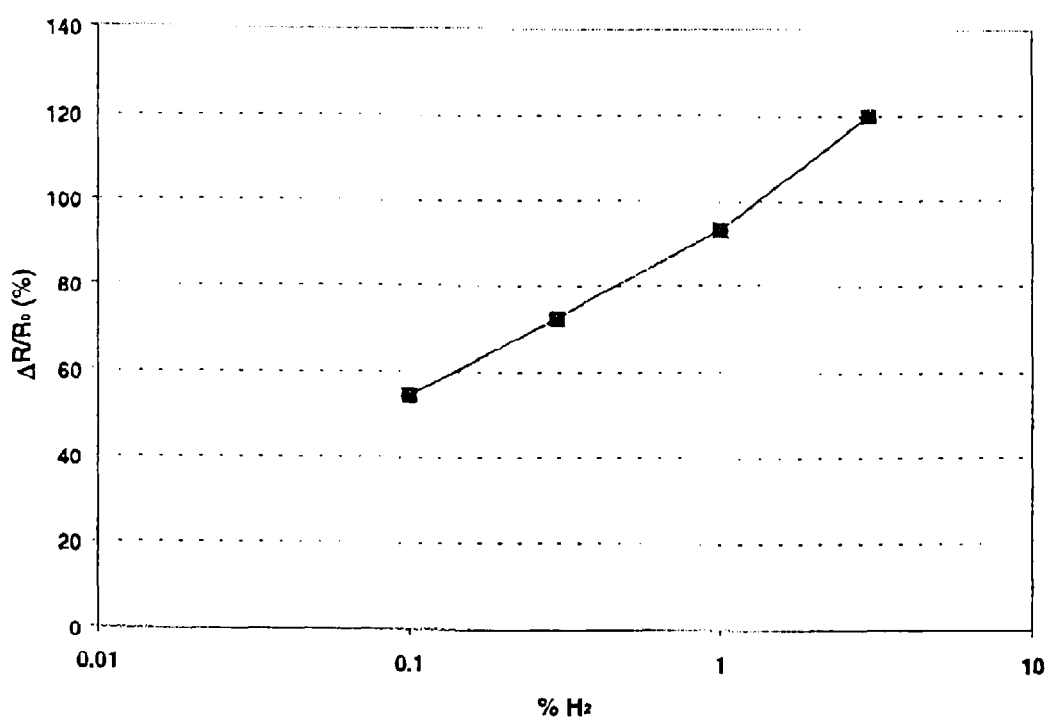
FIG. 7 is a graph showing the resistance response of a palladium/yttrium micro-hotplate sensor as a function of hydrogen concentration, for hydrogen exposures carried out in a background gas of 1 atmosphere of nitrogen.

FIG. 7 is graph of the response of a $H_2$ sensor including a 15 nm layer of palladium deposited on 300 nm of yttrium, overlaid on a suspended microhotplate structure, as a function on $H_2$ concentration. The testing was done at atmospheric pressure, in a nitrogen ambient and the microhotplate element was held at a temperature of ~400° C. The response of the sensor is approximately linear with respect to the log of the $H_2$ concentration over the range tested, viz., 0.1% to 4% $H_2$. The character of such response suggests that such range could readily be extended from 0.01 to 10% of the range that was tested, which is a dynamic range of 3 orders of magnitude.

The features and advantages of the present invention are more fully shown by the following non-limiting examples.

EXAMPLE 1

Thin Film Deposition of Yttrium by Physical Vapor Deposition

Vacuum refined yttrium lumps (99.9%) and palladium pellets (99.9%) were melted in an electron beam PVD tool and used as targets. Depositions were carried out on polished, high grade, quartz photomask blanks. A deposition methodology was established by trial and error that ensured the exclusion of oxygen and moisture in the deposition chamber. A 150 Å thick layer of Pd was determined to be necessary to protect the sensory yttrium layer.

An AFM topographical image of one of the films showed that the root mean square (RMS) roughness of the Pd protective overlayer was 10.8 nm which was more than that of the film grown by CVD (2.5 nm). The $R_{max}$ of the film grown by PVD was also more than that of the film grown by CVD. Nevertheless, films grown by PVD are visibly smooth and reflective, in relation to the films grown by CVD.

EXAMPLE 2

Effects of Exposure of Rare Earth Metal Thin Films to Hydrogen

Strips of rare earth metal thin films were placed in a 1-inch diameter quartz CVD tube and exposed to slightly less than one atmosphere (700 Torr) of hydrogen. The color of the film turned yellowish within 2–3 minutes, indicating the permanent conversion of Y to $YH_2$. Within a minute of this color change the film displayed a striking change in optical transmission, changing from opaque and reflective to transparent. This optical change is reversible and provides a reversible hydrogen sensor. Upon removal of hydrogen an immediate loss of transparency was noted although complete opacity was restored after only several hours. This demonstrates the suitability of rare earth metal thin films for inexpensive, hydrogen-specific, optical sensors in accordance with the present invention.

EXAMPLE 3

Hydrogen Selectivity of Rare Earth Metal Thin Films

A series of film growth experiments was carried out to determine the effect of film thickness both on stress and on the sensory properties of the film. Three sets of films (4 each) with yttrium thicknesses of 2500, 4000 and 5000 Å were grown. Each film had a 150 D Pd protective overlayer deposited thereon.

The selectivity of the sensor was demonstrated by optical change from opaque to clear when the films were exposed to:
1) hydrogen diluted in 50% nitrogen;
2) hydrogen-saturated pentane vapors, thereby presenting hydrogen to the sensor in a low boiling organic solvent; and
3) hydrogen diluted with 50% ammonia.

These results demonstrated the selectivity of the sensor of the present invention. We are unaware of any commercially available sensor that can detect hydrogen under any of the above conditions (1)–(3).

EXAMPLE 4

Fabrication and Testing of Rare-Earth Coated Microhoplate $H_2$ Gas Sensor

Microhotplate structures were fabricated through a commercial foundry and the as-received die was micromachined using $XeF_2$ as a silicon selective etchant. A photolithographic lift-off process was used in combination with physical vapor deposition (PVD) to sequentially deposit yttrium thin films overlaid by palladium on the suspended microhotplate structures. Vacuum refined yttrium lumps (99.9%) and palladium pellets (99.9%) were melted in an electron beam deposition tool and used as targets. The EDS spectrum of the films clearly indicated the presence of both yttrium and palladium on the microhotplates. These devices were wirebonded and packaged in 40 pin ceramic chip carriers.

The fully packaged chips were placed in a sealed chamber, and electrical contact made via feedthroughs into the chamber. Nitrogen and hydrogen were introduced into the chamber and controlled with mass flow controllers and actuated valves. The resistance of the sensing film was measured periodically with a digital multimeter and logged on a desktop computer. A DC power supply was used to heat the microhotplates. It was found that these devices have a significant resistive response to hydrogen in the absence of oxygen. Both the magnitude and speed of this response was found to depend on temperature, thus indicating the value of the micro-hotplate platform. Changes in resistance of greater than 110% were observed in hydrogen concentrations of 3%. Extrapolation of responses measured over a decade of hydrogen concentrations, (0.1%–3%) suggests that better than 100 ppm sensitivity is achievable. The lowest rise and fall times measured were 30 and 300 s respectively.

While the invention has been described herein with reference to various illustrative aspects, features and embodiments, it will be recognized that the invention is not thus limited, but rather encompasses numerous other variations, modifications and other embodiments, as will readily suggest themselves to those of ordinary skill in the art, based on the disclosure and examples herein. Accordingly, the invention is to be broadly construed and interpreted, with respect to the ensuing claims, as including all such variations, modifications and other embodiments within its spirit and scope.

What is claimed is:

1. A hydrogen sensor, comprising:
    at least one hydrogen-interactive thin film sensor element comprising a rare earth metal or a rare earth metal dihydride;
    at least one micro-hotplate structure coupled to said hydrogen-interactive sensor element for selective heating of the sensor element; and
    a hydrogen-permeable material overlaying each hydrogen-interactive sensor element for selective permeation of hydrogen.

2. The hydrogen sensor of claim 1, wherein the rare earth metal or rare earth metal dihydride of the hydrogen-interactive sensor element comprises at least one rare earth metal component selected from the group consisting of trivalent rare earth metals that react with hydrogen to form both metal dihydride and metal trihydride reaction products, wherein the metal dihydride and metal trihydride reaction products have differing physical properties.

3. The hydrogen sensor of claim 1, wherein the hydrogen-interactive thin film sensor element comprises at least one thin film layer comprising one or more metals, present in elemental metal form and/or in a dihydride thereof, wherein the metal is selected from the group consisting of:
    magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof.

4. The hydrogen sensor of claim 1, further including a monitor operatively arranged in monitoring relationship to the hydrogen-interactive thin film sensor element to provide an output indicative of the presence of hydrogen.

5. The hydrogen sensor of claim 1, further including an electrical resistance monitor operatively arranged in monitoring relationship to the hydrogen-interactive thin film sensor element to provide an output indicative of the presence of hydrogen in an environment in contact with the hydrogen-interactive thin film sensor element.

6. The hydrogen sensor of claim 1, wherein the hydrogen-interactive thin film sensor element is formed of a material consisting essentially of rare earth metal dihydride of one or more trivalent rare earth metals, wherein said rare earth metal dihydride is reversibly reactive with hydrogen to form corresponding metal trihydride exhibiting a detectable change of physical properties.

7. The hydrogen sensor of claim 1, wherein the hydrogen-permeable material is selected from the group consisting of palladium, platinum, iridium, silver, gold, cobalt, and alloys thereof.

8. The hydrogen sensor of claim 1, wherein the micro-hotplate structure is controlled by a predetermined time-temperature program for cyclic heating of the hydrogen-interactive thin film gas sensor element by the micro-hotplate structure.

9. The hydrogen sensor of claim 1, wherein said hydrogen-interactive thin film has a thickness of from about 50 to about 2000 nm.

10. The hydrogen sensor of claim 1, wherein the hydrogen-permeable material is in the form of a thin film.

11. The hydrogen sensor of claim 10, wherein the hydrogen-permeable thin film has a thickness of from about 2 to about 1000 nm.

12. The hydrogen sensor of claim 1, wherein the hydrogen-interactive thin film sensor element comprises a rare earth metal thin film that is doped with a dopant.

13. The hydrogen sensor of claim 12, wherein said dopant is selected from the group consisting of magnesium, calcium, strontium, barium, and any combination thereof.

14. The hydrogen sensor of claim 12, wherein said dopant is deposited on the hydrogen-interactive thin film.

15. A hydrogen sensor according to claim 1, comprising a plurality of hydrogen-interactive thin films.

16. A hydrogen sensor according to claim 15, wherein at least two hydro-interactive thin film sensor elements are covered by hydrogen-permeable material of different thickness.

17. A hydrogen sensor according to claim 15, wherein at least two hydrogen-interactive films are differing materials.

18. The hydrogen sensor of claim 1, wherein the rare earth metal or rare earth metal dihydride of the hydrogen-interactive sensor element, arranged for exposure to an environment susceptible to the incursion or generation of hydrogen exhibits a detectable change of physical property when exposed to hydrogen.

19. The hydrogen sensor of claim 18, wherein said detectable change of physical property is selected from the group consisting of optical transmissivity, electrical resistivity, electrical conductivity, electrical capacitance, magneto-resistance and photoconductivity.

20. The hydrogen sensor of claim 18, further comprising a detector constructed and arranged to convert said detectable change of physical property to a perceivable output selected from the group consisting of visual outputs, auditory outputs, tactile outputs, and auditory outputs.

21. The hydrogen sensor of claim 18, wherein said detectable change of physical property comprises a change of electrical property when the hydrogen-interactive thin film sensor element is contacted with hydrogen gas.

22. The hydrogen sensor of claim 18, wherein said detectable change of physical property comprises a change from a metallic state to a semiconducting state.

23. The hydrogen sensor of claim 18, wherein the hydrogen-interactive thin film sensor element comprises yttrium, and the physical property change comprises a change of electrical conductivity or resistivity when the hydrogen-interactive thin film sensor element is contacted with hydrogen gas.

24. A hydrogen sensor device, comprising:
a hydrogen-interactive thin film sensor element comprising a rare earth metal and/or a rare earth metal dihydride;
a micro-hotplate structure coupled to said hydrogen-interactive sensor element for selective heating of the sensor element;
a hydrogen-permeable material overlaying said hydrogen-interactive sensor element for selective permeation of hydrogen; and
a detector coupled with said hydrogen-interactive sensor element for sensing a detectable change of physical property of the sensor element on exposure to hydrogen and generating a correlative output indicative of hydrogen presence.

25. The hydrogen sensor device of claim 24, wherein said detectable change of physical property is selected from the group consisting of optical transmissivity, electrical resistivity, electrical conductivity, electrical capacitance, magneto-resistance and photoconductivity.

26. The hydrogen sensor device of claim 24, wherein the detector is constructed and arranged to convert said detectable change of physical property to a perceivable output selected from the group consisting of visual outputs, auditory outputs, tactile outputs, and auditory outputs.

27. The hydrogen sensor device of claim 24, wherein the rare earth metal or rare earth metal dihydride of the hydrogen-interactive sensor element comprises at least one rare earth metal component, in an elemental metal form and/or in a metal dihydride thereof, selected from the group consisting of trivalent rare earth metals that react with hydrogen to form both metal dihydride and metal trihydride reaction products, wherein the metal dihydride and metal trihydride reaction products have differing physical properties.

28. The hydrogen sensor device of claim 24, wherein the rare earth metal and/or rare earth metal dihydride of the hydrogen-interactive sensor element comprises one or more metals, in elemental metal form and/or in a corresponding metal dihydride, selected from the group consisting of:
magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys containing one or more of such metals.

29. The hydrogen sensor device according to claim 24, further comprising a power supply for the device.

30. The hydrogen sensor device according to claim 29, wherein the power supply is constructed and arranged for actuating the micro-hotplate structure during and/or subsequent to sensing the detectable change of physical property of the hydrogen-interactive thin film gas sensor element in exposure to hydrogen.

31. The hydrogen sensor device according to claim 28, wherein the power supply is constructed and arranged for energizing the detector.

32. A method of fabricating a hydrogen sensor on a substrate, comprising:
constructing on the substrate a micro-hotplate structure; and
forming on the micro-hotplate structure a hydrogen-interactive thin film comprising a rare earth metal and/or a rare earth metal dihydride that upon exposure to hydrogen, exhibits a detectable change of at least one physical property, and wherein the hydrogen-interactive thin film is arranged to be heated by the micro-hotplate structure and forming on the hydrogen-interactive thin film a protective overlayer comprising a hydrogen-permeable material for selective permeation of hydrogen.

33. The method of claim 32, further comprising coupling the hydrogen-interactive thin film with a detector for outputting the detectable change of physical property of the hydrogen-interactive thin film when the hydrogen-interactive thin film is exposed to hydrogen.

34. The method of claim 32, wherein the hydrogen-interactive thin film comprises a rare earth metal component, in elemental metal form and/or in a corresponding metal dihydride, selected from the group consisting of trivalent rare earth metals that react with hydrogen to form both metal dihydride and metal trihydride reaction products, wherein the metal dihydride and metal trihydride reaction products have differing physical properties.

35. The method of claim 32, wherein the hydrogen-interactive thin film comprises one or more metal components, in elemental metal form and/or in a corresponding metal dihydride, selected from the group consisting of:

magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys containing one or more of such metals.

36. The method of claim 32, further comprising coupling the hydrogen-interactive thin film with an electrical resistance monitor to provide an output indicative of the presence of hydrogen in an environment in contact with the rare earth metal thin film.

37. The method of claim 32, wherein the hydrogen-permeable material comprises a metal selected from the group consisting of palladium, platinum, iridium, silver, gold, cobalt, and alloys thereof.

38. The method of claim 32, wherein the hydrogen-interactive thin film comprises a metal selected from the group consisting of lanthanum and yttrium, and the hydrogen-interactive thin film is formed on the substrate by chemical vapor deposition utilizing a corresponding precursor, wherein said precursor is selected from the group consisting of tris(cyclopentadienyl)lanthanum, tris(cyclopentadienyl)yttrium, β-ketoamine complexes of lanthanum, β-ketoamine complexes of yttrium, β-diketonate complexes of lanthanum, β-diketonate complexes of yttrium, β-diiminate complexes of lanthanum, β-diiminate complexes of yttrium; lanthanum amides, and yttrium amides.

39. The method of claim 32, wherein the hydrogen-interactive thin film comprises yttrium, formed on the substrate by chemical vapor deposition utilizing as a precursor $Y(NSiMe_3)_3$.

40. The method of claim 32, wherein the hydrogen-interactive thin film is doped with a dopant.

41. The method of claim 40, wherein the dopant is deposited on the hydrogen-interactive thin film from a precursor, and said precursor is selected from the group consisting of $Mg(thd)_2$, $Ca(thd)_2$, dimethyl aluminumhydride, $Ba(thd)_2$, $Sr(thd)_2$, (COD)Ir(hfac) and $Co(thd)_2$.

42. A method of detecting hydrogen in an environment, comprising:

providing a hydrogen sensor device comprising a hydrogen-interactive thin film a micro-hotplate structure operatively coupled with the hydrogen-interactive thin film for selective heating of the hydrogen-interactive thin film, and a hydrogen-permeable material overlaying the hydrogen-interactive thin film for selective permeation of hydrogen, wherein said hydrogen-interactive thin film is arranged for exposure to the environment and exhibits a detectable change of physical property when the hydrogen-interactive thin film is exposed to hydrogen;

exposing the hydrogen-interactive thin film to the environment;

outputting said detectable change of physical property when the presence of hydrogen in the environment is detected; and selectively heating the hydrogen-interactive thin film by the micro-hotplate structure to enhance the performance of the hydrogen-interactive thin film for detection of hydrogen.

43. The method of claim 42, wherein the hydrogen-interactive thin film comprises one or more metals selected from the group consisting of:

magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys containing one or more of such metals.

44. The method of claim 42, further comprising the step of doping the hydrogen-interactive thin film with a dopant.

45. The method of claim 44, wherein said dopant is selected from the group consisting of magnesium, calcium, strontium, barium, and any combination thereof.

46. The method of claim 44, wherein the doping comprises depositing the dopant on the hydrogen-interactive thin film.

* * * * *